United States Patent [19]

Evans et al.

[11] Patent Number: 4,571,406

[45] Date of Patent: Feb. 18, 1986

[54] ANTI-HYPERTENSIVE CHROMANS AND CHROMENES

[75] Inventors: John M. Evans, Roydon; Frederick Cassidy, Harlow, both of England

[73] Assignee: Beecham Group p.l.c., England

[21] Appl. No.: 610,623

[22] Filed: May 16, 1984

[30] Foreign Application Priority Data

May 18, 1983 [GB] United Kingdom ............... 8313687
Dec. 23, 1983 [GB] United Kingdom ............... 8334418

[51] Int. Cl.$^4$ ................. A61K 31/35; C07D 311/02
[52] U.S. Cl. .................................. 514/456; 514/242;
514/241; 514/444; 549/404; 549/399; 514/443;
549/345; 549/60; 514/422; 549/57; 549/55;
514/414; 549/54; 549/52; 514/409; 549/51;
548/525; 514/397; 548/454; 548/407; 514/380;
548/336; 548/236; 514/378; 548/216; 548/214;
514/377; 548/213; 548/189; 514/376; 548/188;
548/147; 514/374; 548/136; 548/134; 514/372;
548/130; 548/129; 514/371; 548/128; 548/127;
514/370; 546/269; 544/405; 514/369; 544/333;
544/298; 514/365; 544/240; 544/239; 514/363;
544/238; 544/230; 514/362; 514/361; 514/337;
514/314; 514/313; 514/312; 514/307; 514/278;
514/275; 514/274; 514/272; 514/269; 514/256;
514/255; 514/247

[58] Field of Search ............... 544/230, 238, 239, 240,
544/298, 333, 405; 546/269; 548/127, 128, 129,
130, 134, 136, 147, 188, 189, 213, 214, 216, 236,
336, 407, 454, 525; 549/51, 52, 54, 55, 57, 60,
399, 404, 345; 424/283; 514/456, 444, 443, 422,
414, 409, 397, 380, 378, 377, 376, 374, 372, 371,
370, 369, 365, 337, 314, 313, 312, 307, 278, 275,
274, 272, 269, 256, 255, 247, 242, 241, 361, 362,
363

[56] References Cited

U.S. PATENT DOCUMENTS 4,363,811 12/1982 Evans et al. ..................... 548/525
4,366,163 12/1982 Evans et al. ..................... 546/196
4,446,113 5/1984 Evans et al. ..................... 424/267

FOREIGN PATENT DOCUMENTS 46652 3/1982 European Pat. Off. ............ 549/399

OTHER PUBLICATIONS

Lap et al., Aust. J. Chem., 1979, 32 pp. 619-636.

Primary Examiner—Nicky Chan
Attorney, Agent, or Firm—Jacobs & Jacobs

[57] ABSTRACT

Compounds of formula (I):

$$R_8-N-CX-R_7$$
(with $R_1$, $R_2$ on benzene ring, $R_6$, $R_5$, $R_3$, $R_4$ substituents and O in ring) (I)

wherein:
either one of $R_1$ and $R_2$ is hydrogen and the other is selected from the class of $C_{1-6}$ alkylcarbonyl, $C_{1-6}$ alkoxycarbonyl, $C_{1-6}$ alkylcarbonyloxy, $C_{1-6}$ alkylhydroxymethyl, nitro, cyano, chloro, trifluoromethyl, $C_{1-6}$ alkylsulphinyl, $C_{1-6}$ alkylsulphonyl, $C_{1-6}$ alkoxysulphinyl, $C_{1-6}$ alkoxysulphonyl, $C_{1-6}$ alkylcarbonylamino, $C_{1-6}$ alkoxycarbonylamino, $C_{1-6}$ alkylthiocarbonyl, $C_{1-6}$ alkoxy-thiocarbonyl, $C_{1-6}$ alkylthiocarbonyloxy, 1-mercapto $C_{2-7}$ alkyl, formyl or aminosulphinyl, aminosulphonyl or aminocarbonyl, the amino moiety being optionally substituted by one or two $C_{1-6}$ alkyl groups, or $C_{1-6}$ alkylsulphinylamino, $C_{1-6}$ alkylsulphonylamino $C_{1-6}$ alkoxysulphinylamino or $C_{1-6}$ alkoxysulphonylamino, or ethylenyl terminally substituted by $C_{1-6}$ alkylcarbonyl, nitro or cyano, or —C($C_{1-6}$ alkyl)NOH or —C($C_{1-6}$ alkyl)NNH$_2$, or one of $R_1$ and $R_2$ is nitro, cyano or $C_{1-3}$ alkylcarbonyl and the other is methoxy or amino optionally substituted by one or two $C_{1-6}$ alkyl or by $C_{2-7}$ alkanoyl;
one of $R_3$ and $R_4$ is hydrogen or $C_{1-4}$ alkyl and the other is $C_{1-4}$ alkyl or $R_3$ and $R_4$ together are $C_{2-5}$ polymethylene;
either $R_5$ is hydrogen, hydroxy, $C_{1-6}$ alkoxy or $C_{1-7}$ acyloxy and $R_6$ is hydrogen or $R_5$ and $R_6$ together are a bond;
$R_7$ is aryl or heteroaryl, either being optionally substituted by one or more groups or atoms selected from the class of $C_{1-6}$ alkyl, $C_{1-6}$ alkoxy, hydroxy, halogen, trifluoromethyl, nitro, cyano, $C_{1-12}$ carboxylic acyl, or amino or aminocarbonyl optionally substituted by one or two $C_{1-6}$ alkyl;
$R_8$ is hydrogen or $C_{1-6}$ alkyl; and
X is oxygen or sulphur; the $R_8$—N—CX—$R_7$ group being trans to the $R_5$ group when $R_5$ is hydroxy, $C_{1-6}$ alkoxy or $C_{1-7}$ acyloxy; or a pharmaceutically acceptable salt or solvate thereof, have antihypertensive activity.

24 Claims, No Drawings

ANTI-HYPERTENSIVE CHROMANS AND CHROMENES

The present invention relates to novel chromans and chromenes having pharmacological activity, to a process for preparing them, to pharmaceutical compositions containing them, and to their use in the treatment of mammals.

U.S. Pat. Nos. 4,110,347 and 4,119,643 and 4,251,537 and European Patent Publications Nos. 28 064 and 28 449 disclose classes of chromans that are described as having blood pressure lowering activity or anti-hypertensive activity.

European Patent Publication No. 76 075 discloses a further class of chromans that are substituted in the 4-position by a piperidonyl or pyrrolidonyl group. Such chromans are also described as having blood pressure lowering activity.

A further class of chromans, and their corresponding chromenes, has now been discovered which are characterised by the presence of an arylcarbonylamino or aryl-thiocarbonylamino group or an heteroarylcarbonylamino or heteroaryl-thiocarbonylamino group that substitutes the chroman or chromene in the 4-position. In addition, such chromans and chromenes have been found to have blood pressure lowering activity.

Accordingly, the present invention provides a compound of formula (I):

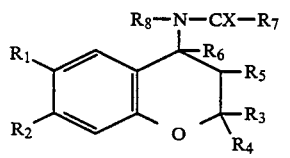

wherein:

either one of $R_1$ and $R_2$ is hydrogen and the other is selected from the class of $C_{1-6}$ alkylcarbonyl, $C_{1-6}$ alkoxycarbonyl, $C_{1-6}$ alkylcarbonyloxy, $C_{1-6}$ alkylhydroxymethyl, nitro, cyano, chloro, trifluoromethyl, $C_{1-6}$ alkylsulphinyl, $C_{1-6}$ alkylsulphonyl, $C_{1-6}$ alkoxysulphinyl, $C_{1-6}$ alkoxysulphonyl, $C_{1-6}$ alkylcarbonylamino, $C_{1-6}$ alkoxycarbonylamino, $C_{1-6}$ alkyl-thiocarbonyl, $C_{1-6}$ alkoxy-thiocarbonyl, $C_{1-6}$ alkyl-thiocarbonyloxy, 1-mercapto $C_{2-7}$ alkyl, formyl, or aminosulphinyl, aminosulphonyl or aminocarbonyl, the amino moiety being optionally substituted by one or two $C_{1-6}$ alkyl groups, or $C_{1-6}$ alkylsulphinylamino, $C_{1-6}$ alkylsulphonylamino, $C_{1-6}$ alkoxysulphinylamino or $C_{1-6}$ alkoxysulphonylamino, or ethylenyl terminally substituted by $C_{1-6}$ alkylcarbonyl, nitro or cyano, or —C($C_{1-6}$ alkyl)NOH or —C($C_{1-6}$ alkyl)NNH$_2$, or one of $R_1$ and $R_2$ is nitro, cyano or $C_{1-3}$ alkylcarbonyl and the other is methoxy or amino optionally substituted by one or two $C_{1-6}$ alkyl or by $C_{2-7}$ alkanoyl;

one of $R_3$ and $R_4$ is hydrogen or $C_{1-4}$ alkyl and the other is $C_{1-4}$ alkyl or $R_3$ and $R_4$ together are $C_{2-5}$ polymethylene;

either $R_5$ is hydrogen, hydroxy, $C_{1-6}$ alkoxy or $C_{1-7}$ acyloxy and $R_6$ is hydrogen or $R_5$ and $R_6$ together are a bond;

$R_7$ is aryl or heteroaryl, either being optionally substituted by one or more groups or atoms selected from the class of $C_{1-6}$ alkyl, $C_{1-6}$ alkoxy, hydroxy, halogen, trifluoromethyl, nitro, cyano, $C_{1-12}$ carboxylic acyl, or amino or aminocarbonyl optionally substituted by one or two $C_{1-6}$ alkyl;

$R_8$ is hydrogen or $C_{1-6}$ alkyl; and

X is oxygen or sulphur; the $R_8$—N—CS—$R_7$ group being trans to the $R_5$ group when $R_5$ is hydroxy, $C_{1-6}$ alkoxy or $C_{1-7}$ acyloxy; or a pharmaceutically acceptable salt or solvate thereof.

When one of $R_1$ and $R_2$ is hydrogen, the other is, preferably, selected from the class of $C_{1-6}$ alkylcarbonyl, $C_{1-6}$ alkoxycarbonyl, nitro or cyano. In particular, when one of $R_1$ and $R_2$ is hydrogen, the other is, preferably, acetyl, nitro or cyano, especially nitro or cyano.

When one of $R_1$ and $R_2$ is hydrogen, it is preferred that $R_2$ is hydrogen.

When one of $R_1$ and $R_2$ is nitro, cyano or $C_{1-3}$ alkylcarbonyl the other is, preferably, amino optionally substituted by one or two $C_{1-6}$ alkyl or by $C_{2-7}$ alkanoyl. In particular, when one of $R_1$ and $R_2$ is nitro, cyano or $C_{1-3}$ alkylcarbonyl, the other is amino, methylamino, dimethylamino or acetylamino. Most preferably, one of $R_1$ and $R_2$ is nitro or cyano, especially cyano, and the other is amino.

When one of $R_1$ and $R_2$ is nitro, cyano or $C_{1-3}$ alkylcarbonyl, it is preferred that $R_1$ is nitro, cyano or $C_{1-3}$ alkylcarbonyl.

The alkyl groups or alkyl moieties of alkyl-containing groups for $R_1$ or $R_2$ are, preferably, methyl or ethyl.

Preferably, $R_3$ and $R_4$ are both $C_{1-4}$ alkyl, in particular both methyl.

When $R_5$ is $C_{1-6}$ alkoxy and $R_6$ is hydrogen, preferred examples of $R_5$ include methoxy and ethoxy, of which methoxy is more preferred. When $R_5$ is $C_{1-7}$ acyloxy and $R_6$ is hydrogen, a preferred class of $R_5$ is unsubstituted carboxylic acyloxy, such as unsubstituted aliphatic acyloxy or benzoyloxy. However, it is preferred that $R_5$ and $R_6$ together are a bond, or $R_5$ and $R_6$ are both hydrogen, or, in particular, that $R_5$ is hydroxy and $R_6$ is hydrogen.

Examples of aryl include phenyl and naphthyl of which phenyl is preferred.

A sub-class of heteroaryl is 5- or 6-membered monocyclic or 9- or 10-membered bicyclic heteroaryl of which 5- or 6-membered monocyclic heteroaryl is preferred. In addition, 5- or 6-membered monocyclic or 9- or 10-membered bicyclic heteroaryl preferably contains one, two or three heteroatoms which are selected from the class of oxygen, nitrogen and sulphur and which, in the case of there being more than one heteroatom, are the same or different.

Examples of 5- or 6-membered monocyclic heteroaryl containing one, two or three heteroatoms which are selected from the class of oxygen, nitrogen and sulphur include furanyl, thiophenyl, pyrryl, oxazolyl, thiazolyl, imidazolyl and thiadiazolyl, and pyridinyl, pyridazinyl, pyrimidinyl, pyrazinyl and triazinyl. Preferred examples of such groups include furanyl, thiophenyl, pyrryl and pyridyl, in particular 2- and 3-furanyl, 2- and 3-pyrryl, 2- and 3-thiophenyl, and 2-, 3- and 4-pyridinyl.

Examples of 9- or 10-membered bicyclic heteroaryl containing one, two or three heteroatoms which are selected from the class of oxygen, nitrogen and sulphur include benzofuranyl, benzothiophenyl, indolyl and indazolyl, quinolinyl and isoquinolinyl, and quinazoninyl. Preferred examples of such groups include 2- and 3-benzofuranyl, 2- and 3-benzothiophenyl, and 2- and 3-indolyl, and 2- and 3-quinolinyl.

Preferably, the number of groups or atoms for optional substitution of aryl or heteroaryl is one, two, three or four.

Preferred examples of the groups or atoms for optional substitution of aryl or heteroaryl include methyl, methoxy, hydroxy, chloro, nitro or cyano.

A sub-class of $R_7$ is phenyl or naphthyl or a 5- or 6-membered monocyclic or a 9- or 10-membered bicyclic heteroaryl, the phenyl or heteroaryl group being optionally substituted by one, two, three or four groups or atoms selected from the class of $C_{1-6}$ alkyl, $C_{1-6}$ alkoxy, halogen, trifluoromethyl, nitro or cyano.

A preferred sub-class of phenyl optionally substituted as hereinbefore defined is phenyl, 4-substituted phenyl, 3-substituted phenyl, 3,4-disubstituted phenyl and 3,4,5-trisubstituted phenyl. Particular examples of phenyl optionally substituted as hereinbefore defined include phenyl, 4-hydroxyphenyl, 4-fluorophenyl, 4-cyanophenyl, 3-nitrophenyl, 3,4-dichlorophenyl and 3,4,5-trimethoxyphenyl.

A preferred sub-class of 5- or 6-membered monocyclic or 9- or 10-membered bicyclic heteroaryl optionally substituted as hereinbefore defined is unsubstituted or mono-substituted 5- or 6-membered monocyclic or 9- or 10-membered bicyclic heteroaryl, in particular unsubstituted 5- or 6-membered monocyclic or 9- or 10-membered bicyclic heteroaryl.

Examples of $R_8$ include hydrogen, methyl, ethyl, n- or iso-propyl. Preferably, $R_8$ is hydrogen or methyl, especially hydrogen.

Examples of a pharmaceutically acceptable salt of a compound of formula (I) include the acid addition salts of a compound of formula (I), wherein one or other of $R_1$ and $R_2$ is amino or an amino-containing group, or wherein amino is an optional substituent of aryl or heteroaryl, for example the hydrochloride and hydrobromide salts.

Examples of a pharmaceutically acceptable solvate of a compound of formula (I) include the hydrate.

Preferably, a compound of formula (I) is in substantially pure form.

The compounds of formula (I), wherein $R_5$ is hydrogen, hydroxy, $C_{1-6}$ alkoxy or $C_{1-7}$ acyloxy and $R_6$ is hydrogen, are asymmetric and, therefore, can exist in the form of optical isomers. The present invention extends to all such isomers individually and as mixtures, such as racemic modifications.

Examples of compounds of formula (I) include the compounds prepared in the Examples hereinafter. Preferred examples include the compounds of Examples 1,3,5,7,8,9,10 and 13.

The present invention also provides a process for preparing a compound of formula (I), which comprises acylating a compound of formula (II):

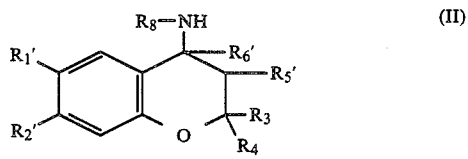

(II)

wherein $R_1'$ and $R_2'$ are $R_1$ and $R_2$, as defined hereinbefore, or a group or atom convertible thereto, $R_3$, $R_4$ and $R_8$ are as defined hereinbefore, $R_5'$ is hydroxy, $C_{1-6}$ alkoxy or $C_{1-7}$ acyloxy and $R_6'$ is hydrogen, the $R_8NH$ group being trans to the $R_5'$ group, with an acylating agent of formula (III):

$$R_7\text{—CO—}L_1 \qquad \text{(III)}$$

wherein $R_7$ is as defined hereinbefore and $L_1$ is a leaving group; in the case where $R_1'$ or $R_2'$ is a group or atom convertible into $R_1$ or $R_2$, converting the group or atom into $R_1$ or $R_2$; optionally converting $R_1$, $R_2$ or $R_5$ in the resulting compound of formula (I) into another $R_1$, $R_2$ or $R_5$; in the case where $R_5$ and $R_6$ in the resulting compound of formula (I) are hydroxy and hydrogen respectively, optionally dehydrating the compound to give another compound of formula (I), wherein $R_5$ and $R_6$ together are a bond, and optionally reducing the resulting compound of formula (I), wherein $R_5$ and $R_6$ together are a bond, to give another compound of formula (I), wherein $R_5$ and $R_6$ are both hydrogen; optionally thiating the $R_8$—N—CO—$R_7$ group in the resulting compound of formula (I) to give another compound of formula (I), wherein X is sulphur; and optionally forming a pharmaceutically acceptable salt or solvate.

The leaving group ($L_1$) is a group that is displaceable by a primary or secondary amino nucleophile. Examples of such a group include $C_{1-4}$ alkylcarbonyloxy and halogen, such as chloro and bromo. When the leaving group ($L_1$) is any of these examples, the acylating agent of formula (III) is either an acid anhyride or an acid halide. When it is an acid anhydride, it is, preferably, a mixed anhyride, which may be prepared in situ from an aromatic or heteroaromatic carboxylic acid and an alkyl chlorocarbonate, such as ethyl chloroformate.

When the acylating agent of formula (III) is an acid anhydride, the acylation of the compound of formula (II) is, preferably, carried out using the anhydride as the solvent in the presence of an acid acceptor, such as sodium acetate.

When the acylating agent of formula (III) is an acid halide, the acylation of the compound of formula (II) is, preferably, carried out in a non-aqueous medium, such as methylene chloride, in the presence of an acid acceptor, such as triethylamine, trimethylamine or pyridine.

When $R_5'$ in a compound of formula (II) is hydroxy, there is a risk of a side-reaction between the hydroxy group and the acylating agent of formula (III). It is, therefore, preferred that the reaction is carried out under controlled conditions such that only the amine, $R_8NH$—, is acylated.

Conversions of an aromatic group into $R_1$ or $R_2$, as defined hereinbefore, are generally known in the art of aromatic chemistry. For example, it is preferred when carrying out the acylation of a compound of formula (II), first to protect any unsubstituted terminal amine that may be present for $R_1$ or $R_2$ and afterwards to convert the protected amino moiety into the required terminal amine. Examples of protecting agents include acyl groups, such as acetyl, which may be added and removed conventionally. If it is desired to protect a terminal amino moiety in the presence of a cyano group then a more appropriate method is to use a trifluoroacetyl protecting group which may be removed by mild hydrolysis or to use a benzyloxycarbonyl or a p-nitrobenzyloxycarbonyl protecting group which may be removed by mild catalytic hydrogenolysis.

If the optional thiation reaction is to be carried out in order to obtain a compound of formula (I), wherein one or the other of $R_1$ and $R_2$ is a carbonyl-containing group and X is sulphur, it is preferred to use in the acylation reaction the corresponding compound of formula (II), wherein $R_1'$ or $R_2'$ is a protected carbonyl-containing group, and after thiation to convert the protected carbonyl-containing group into the required carbonyl-containing group for $R_1$ or $R_2$. Examples of preferred carbonyl protecting groups include ketalising agents, which may be added and removed in conventional manner.

Examples of an optional conversion of $R_1$ or $R_2$ in the resulting compound of formula (I) into another $R_1$ or $R_2$, as defined hereinbefore, include the optional conversion of an α-hydroxyethyl group into acetyl by oxidation, the optional conversion of an amino group into a chloro atom by diazotisation and reaction with a chloride salt, the optional conversion of an amino group into an amino group substituted by one or two $C_{1-6}$ alkyl or by $C_{2-7}$ alkanoyl, or the optional conversion of a hydrogen atom into a nitro group by nitration.

Examples of an optional conversion of $R_5$ in a compound of formula (I) into another $R_5$ are generally known in the art. For example, when $R_5$ is hydroxy, it may be alkylated using an alkyl iodide in an inert solvent, such as toluene, in the presence of a base, such as potassium hydroxide, or it may be acylated using a carboxylic acid chloride or anhydride in a non-hydroxylic solvent in the pressure of a base, such as trimethylamine, triethylamine or piperidine. alternatively, when $R_5$ is $C_{1-7}$ acyloxy or $C_{1-6}$ alkoxy, it may be converted into hydroxy by conventional hydrolysis with, for example, dilute mineral acid.

The optional dehydration of the resulting compound of formula (I), wherein $R_5$ and $R_6$ are hydroxy and hydrogen respectively, into another compound of formula (I), wherein $R_5$ and $R_6$ together are a bond, may be carried out under conventional dehydration conditions for example, by using a dehydrating agent, such as sodium hydride, in an inert solvent, such as dry tetrahydrofuran, at reflux temperature.

The optional reduction of the resulting compound of formula (I), wherein $R_5$ and $R_6$ together are a bond, into another compound of formula (I), wherein $R_5$ and $R_6$ are both hydrogen, may be carried out by hydrogenation using a catalyst of palladium on charcoal.

The optional thiation of the $R_8$—N—CO—$R_7$ group in a compound of formula (I) to give another compound of formula I, wherein X is sulphur, is, preferably, carried out with conventional thiation agents, such as hydrogen sulphide, phosphorous pentasulphide and Lawesson's reagent (p-methoxyphenylthiophosphine sulphide dimer). The use of hydrogen sulphide and phosporous pentasulphide may lead to side-reactions and, therefore, the use of Lawesson's reagent is preferred.

The thiation reaction conditions are conventional for the thiation agent employed. For example, the use of hydrogen sulphide is, preferably, acid catalysed by, for example, hydrogen chloride in a polar solvent, such as acetic acid or ethanol. The preferred use of Lawesson's reagent is preferably carried out under reflux in a dry solvent, such as toluene or methylene chloride.

The optional formation of a pharmaceutically acceptable salt or solvate may be carried out conventionally.

A compound of formula (II) may be prepared by reacting a compound of formula (IV):

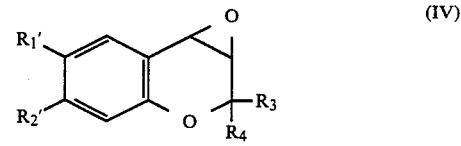

wherein $R_1'$, $R_2'$, $R_3$ and $R_4$ are as defined hereinbefore, with a compound of formula (V):

wherein $R_8$ is as defined hereinbefore; and optionally converting the hydroxy group for $R_5'$ in the resulting compound of formula (II) into a $C_{1-4}$ alkoxy or $C_{1-7}$ acyloxy group.

The reaction is normally carried out in a solvent, such as a $C_{1-4}$ alcohol, in particular methanol, ethanol or propanol at an ambient or an elevated temperature, for example 15° to 100° C. The reaction proceeds particularly smoothly if carried out in ethanol under reflux.

The resulting compound of formula (II) may be removed from the reaction mixture by removal of the solvent, for example, by evaporation under reduced pressure. Any epoxide impurity may be removed conventionally, for example by chromatography.

The optional conversion of the hydroxy group for $R_5'$ in the resulting compound of formula (II) into a $C_{1-6}$ alkoxy or $C_{1-7}$ acyloxy group may be carried out as described hereinbefore in relation to the corresponding conversion of $R_5$ in a compound of formula (I).

A compound of formula (IV) may be prepared, preferably in situ by reacting a compound of formula (VI):

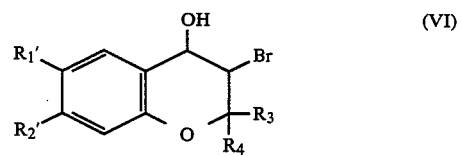

wherein $R_1'$, $R_2'$, $R_3$ and $R_4$ are as defined hereinbefore and the hydroxy group is trans to the bromo atom, with a base, such as potassium hydroxide, in a solvent, such as ether or aqueous dioxan.

Compounds of formula (VI) are known and may be prepared in accordance with any appropriate known process, for example, by the process described in the aforementioned U.S. patents and European patent publications. Schematically, such process can be depicted thus.

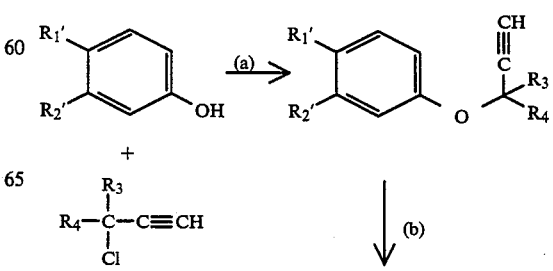

-continued

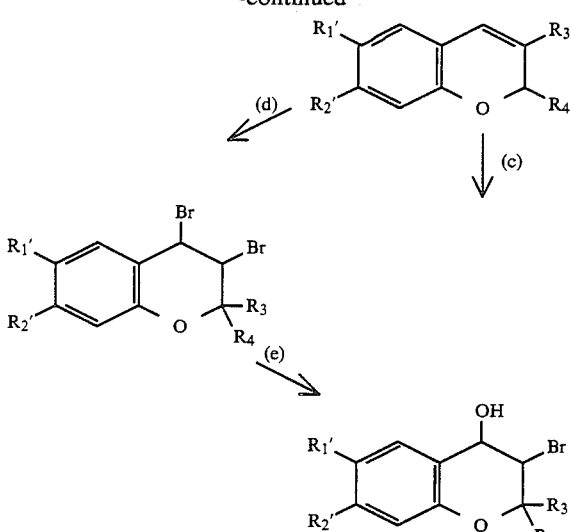

(a) Room temperature; NaOH/40% benzyltrimethylammonium hydroxide in methanol;
(b) Heat in o-dichlorobenzene;
(c) N—bromosuccinimide/dimethylsulphoxide/water;
(d) Bromine in carbon tetrachloride; and
(e) Acetone/water.

The above process may produce mixtures of compounds during reaction (b) owing to the two sites available for ring formation. It is therefore advisable to remove any of the undesired compound by, for example, chromatography, before reaction (c) or (d).

As mentioned previously, the compounds of formula (I), wherein $R_5$ is hydrogen, hydroxy, $C_{1-6}$ alkoxy or $C_{1-7}$ acyloxy and $R_6$ is hydrogen, exist in optically active forms, and the processes of the present invention produce mixtures of such forms. The individual isomers may be separated one from the other by chromatography using a chiral phase.

It is preferred that the compounds of formula (I) are isolated in substantially pure form.

The compounds of formula (II) and (V) are also known or can be prepared analogously to the preparation of known compounds.

As mentioned previously, the compounds of formula (I) have been found to have blood-pressure lowering activity. They are therefore useful in the treatment of hypertension.

The present invention accordingly provides a pharmaceutical composition which comprises a compound of this invention and a pharmaceutically acceptable carrier. In particular, the present invention provides an anti-hypertensive pharmaceutical composition which comprises an anti-hypertensive effective amount of a compound of this invention and a pharmaceutically acceptable carrier.

The compositions are preferably adapted for oral administration. However, they may be adapted for other modes of administration, for example parenteral administration for patients suffering from heart failure.

In order to obtain consistency of administration it is preferred that a composition of the invention is in the form of a unit-dose. Suitable unit dose forms include tablets, capsules and powders in sachets or vials. Such unit dose forms may contain from 1 to 100 mg of a compound of the invention and more usually from 2 to 50 mg, for example 5 and 25 mg such as 6, 10, 15 or 20 mg. Such compositions may be administered from 1 to 6 times a day, more usually from 2 to 4 times a day, in a manner such that the daily dose is from 1 to 200 mg for a 70 mg human adult and more particularly from 1 to 10 mg.

The compositions of the invention may be formulated with conventional excipients, such as a filler, a disintegrating agent, a binder, a lubricant, a flavouring agent and the like. They are formulated in conventional manner, for example in a manner similar to that used for known anti-hypertensive agents, diuretics and β-blocking agents.

The present invention further provides a compound of the invention for use in the treatment or prophylaxis of mammals, especially mammals with hypertension.

The present invention yet further provides a method of treating or preventing hypertension in mammals including man, which comprises administering to the patient an anti-hypertensive effect amount of a compound or a pharmaceutical composition of the invention.

The following descriptions relate to the preparation of intermediates and the following examples relate to the preparation of a compound of formula (I).

EXAMPLE 1

Trans-4-Benzoylamino-6-cyano-3,4-dihydro-2,2-dimethyl-2H-1-benzopyran-3-ol

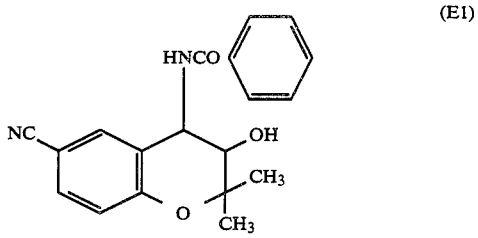

(E1)

Trans-4-amino-6-cyano-3,4-dihydro-2,2-dimethyl-2H-1-benzopyran-3-ol* (436 mg) and sodium hydroxide pellets (80 mg) were stirred in water (20 ml) and chloroform (15 ml) for 0.5 hr under nitrogen at room temperature. Benzoyl chloride (0.255 ml) was added in one portion and the stirring continued for an additional 1 h. The layers were separated and the aqueous layer extracted with chloroform. The combined chloroform extracts were washed with water and brine and dried over anhydrous magnesium sulphate. Filtration and evaporation gave an oil (619 mg) which solidified on standing. Purification by chromatography (chromatotron, ethyl acetate as eluent) and three recrystallisations from ethyl acetate-hexane gave the title compound (120 mg) as crystals of m.p. 192.5°–194° C.

Mass spectrum $M^+ - H_2O$ at M/Z 304.1214. Calcd for $C_{19}H_{18}N_2O_3$: 304.1212.

*The starting material for this and subsequent examples was prepared in accordance with the procedure described in European Patent Publication No. 76 075.

EXAMPLE 2

Trans-4-(4-Cyanobenzoylamino)-6-cyano-3,4-dihydro-2,2-dimethyl-2H-1-benzopyran-3-ol

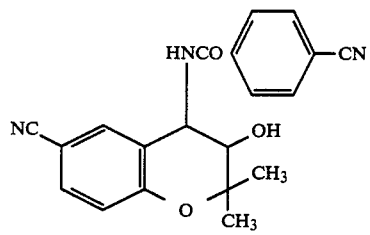
(E2)

Trans-4-amino-6-cyano-3,4-dihydro-2,2-dimethyl-2H-1-benzopyran-3-ol (1.00 g) and triethylamine (0.46 g) were stirred in methylene chloride (30 ml). 4-Cyanobenzoyl chloride (0.76 g) was added in one portion with cooling to 0° C. The reaction mixture was stirred for an additional 1 hr. and allowed to reach room temperature. The solution was washed with water and brine and dried over anhydrous magnesium sulphate. Filtration and evaporation gave a solid which on recrystallisation from ethyl acetate furnished the title compound as crystals (215 mg) of m.p. 260°–262° C.

NMR (DMSOd$_6$) δ:
1.13 (3H,s)
1.53 (3H,s)
3.14 (1H,s)
3.83 (1H,q,J=9,5 Hz)
5.18 (1H,t,J=9,9 Hz)
5.47 (1H,d,J=5 Hz)
6.90 (1H,d,J=10 Hz)
7.45 (1H,q,J=10,2 Hz) overlapped by
7.53 (1H,d,J=2 Hz)
7.80 (2H,d,J=8 Hz)
8.20 (2H,d,J=8 Hz)
8.88 (1H,d,J=9 Hz)

EXAMPLE 3

Trans-6-cyano-3,4-dihydro-2,2-dimethyl-4-(3'-nitrobenzoylamino)-2H-1-benzopyran-3-ol

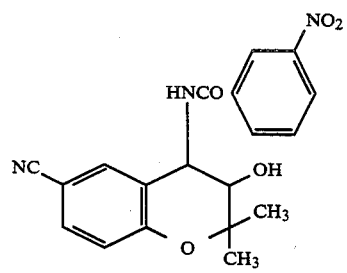
(E3)

Trans-4-amino-6-cyano-3,4-dihydro-2,2-dimethyl-2H-1-benzopyran-3-ol (1.00 g) and triethylamine (0.46 g) stirred in dichloromethane (30 ml) were treated, in an identical manner to that of example (2), with 3-nitrobenzoyl chloride (0.85 g). The crude product was recrystallised from ethyl acetate to give the title compound as crystals (290 mg) of m.p. 218°–220° C.

Mass spectrum M$^+$—H$_2$O at M/Z 349.1063. Calcd. for C$_{19}$H$_{15}$N$_3$O$_4$: 349.1062.

EXAMPLE 4

Trans-4-(3,4-dichlorobenzoylamino)-6-cyano-3,4-dihydro-2,2-dimethyl-2H-1-benzopyran-3-ol

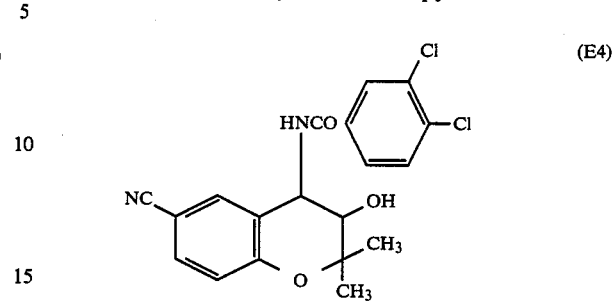
(E4)

Trans-4-amino-6-cyano-3,4-dihydro-2,2-dimethyl-2H-1-benzopyran-3-ol (1.00 g) and triethylamine (0.64 ml) stirred in dichloromethane (25 ml) were treated, in an identical manner to that of example (2), with 3,4-dichlorobenzoylchloride (0.96 g). The crude product was recrystallised from ethyl acetate to give the title compound (0.98 g) as crystals of m.p. 230°–231° C.

NMR (CDCl$_3$+little DMSOd$_6$) δ:
1.29 (3H,s)
1.51 (3H,s)
2.97 (1H,s)
3.82 (1H,q,J=9,5 Hz)
5.17 (1H,t,J=9 Hz) overlapping
5.21 (1H,d,J=5 Hz)
6.85 (1H,d,J=9 Hz)
7.35–7.65 (3H,series of m)
7.92 (1H,q,J=8 Hz)
8.20 (1H,d,J=2 Hz)
8.66 (1H,d,J=9 Hz)

EXAMPLE 5

Trans-6-cyano-4-(2-furoylamino)-3,4-dihydro-2,2-dimethyl-2H-1-benzopyran-3-ol

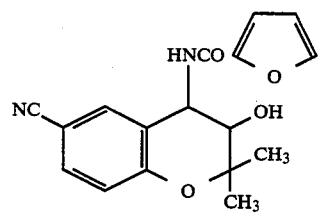
(E5)

Trans-4-amino-6-cyano-3,4-dihydro-2,2-dimethyl-2H-1-benzopyran-3-ol (4.00 g) and triethylamine (2.55 ml) stirred in dichloromethane (120 ml) were treated, in an identical manner to that of example (2), with furoyl chloride (1.80 ml). The crude product was recrystallised from ethyl acetate to give the title compound as crystals (3.13 g) of m.p. 207°–209° C.

NMR (CD$_3$OD) δ:
1.31 (3H,s)
1.53 (3H,s)
3.77 (1H,d,J=10 Hz)
5.19 (1H,d,J=10 Hz)
6.60 (1H,q,J=2,1 Hz)
6.92 (1H,d,J=8 Hz)
7.23 (1H,q,J=2,0.5 Hz)
7.48 (1H,q,J=8,2 Hz) overlapped by
7.50–7.65 (2H,m)

EXAMPLE 6

6-Cyano-3,4-dihydro-2,2-dimethyl-trans-4-(2-naphthoylamino)2H-1-benzopyran-3-ol

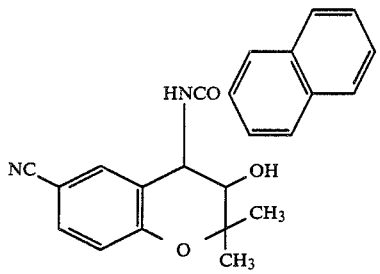
(E6)

The compound of Example 6 was prepared in an analogous manner to that of Example 2. The title compound was recrystallised from ethyl acetate-pentane; m.p. 238°–240° C.

NMR (CD$_3$OD) δ:
1.36 (3H, s)
1.56 (3H, s)
3.88 (1H, d, J=10 Hz)
5.33 (1H, d, J=10 Hz)
6.93 (1H, d, J=9 Hz)
7.40–8.10 (8H, series of m)
8.50 (1H, narrow m)

6-Cyano-3,4-dihydro-2,2-dimethyl-trans-4-(1-naphthoylamino)2H-1-benzoypyran-3-ol is prepared in an analogous manner.

EXAMPLE 7

Trans-6-Cyano-3,4-dihydro-2,2-dimethyl-4-(3-pyridinylcarbonylamino)-2H-1-benzopyran-3-ol

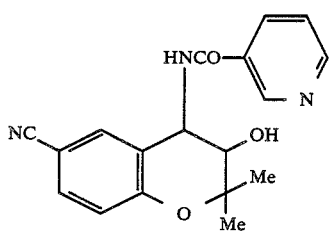
(E7)

To a stirred solution of nicotinic acid (0.57 g) and triethylamine (0.64 mL) in dichloromethane (60 mL), was added ethyl chloroformate (0.47 mL) in dichloromethane (30 mL), followed by trans-4-amino-6-cyano-3,4-dihydro-2,2-dimethyl-2H-1-benzopyran-3-ol (1 g) in dichloromethane (30 ml) during 0.5 h. After the addition was complete the mixture was stirred for a further 18 hours at room temperature. The reaction mixture was washed with water and brine and dried over anh. magnesium sulphate. Filtration and evaporation gave a pale yellow solid (1.36 g). Recrystallisation from ethyl acetate gave starting aminoalcohol (0.50 g). The mother liquids were chromatographed (chromatotron, gradient elution pentaneethyl acetate) and fractions (0.30 g) containing the product were combined. One recrystallisation from ethyl acetate gave the title compound (80 mg) of mp 221°–223° C.

Mass spectrum M+—H$_2$O at m/z 305.1158. Calcd. for C$_{18}$H$_{15}$N$_3$O$_2$ 305.1165.

Anal. Found: C,66.56; H,5.38; N,12.79. Calcd. for C$_{18}$H$_{17}$N$_3$O$_3$: C,66.86; H,5.30; N,13.00%.

EXAMPLE 8

Trans-6-Cyano-3,4-dihydro-2,2-dimethyl-4-(2-pyridinylcarbonylamino)-2H-1-benzopyran-3-ol

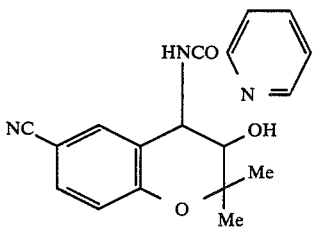
(E8)

The title compound was obtained by the same method as described in Example 6, the acid employed being pyridine-2-carboxylic acid; purification by recrystallisation from ethyl acetate-pentane gave crystals of mp 165° C.

NMR (CDCl$_3$) δ:
1.36 (3H)
1.55 (3H)
3.82 (1H, d, J=10 Hz)
4.00 (1H, exchangeable)
5.26 (1H, t, J=10,9 Hz, collapsing to d, J=10 Hz on addition D$_2$O)
6.93 (1H, d, J=9 Hz)
7.40–7.65 (3H, m)
7.80–8.65 (4H, series of m, 1H exchangeable)

EXAMPLE 9

Trans-6-Cyano-4-(3-furanoylamino)-3,4-dihydro-2,2-dimethyl-2H-1-benzopyran-3-ol (E9)

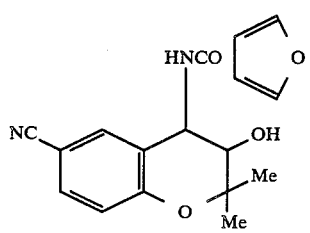
(E9)

Using 3-furoic acid in the method described for Example 6 gave the title compound as crystals of mp 238°–239° C. from chloroform.

NMR (CDCl$_3$/CD$_3$OD) δ:
1.33 (3H)
1.54 (3H)
3.77 (1H, d, J=10 Hz)
5.22 (1H, d, J=10 Hz)
6.80–7.00 (2H, m)
7.40–7.65 (3H, m)
8.16 (1H, narrow m)

EXAMPLE 10

Trans-6-Cyano-3,4-dihydro-2,2-dimethyl-4-(2-pyrrylcarbonylamino)-2H-1-benzopyran-3-ol

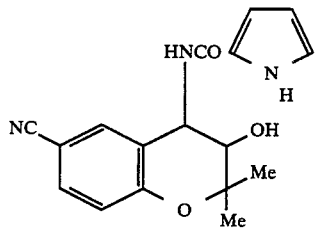
(E10)

To a stirred solution of pyrrole-2-carboxylic acid (1.02 g) in dimethyl formamide (20 mL) cooled in an ice bath, were added dicyclohexylcarbodiimide (1.89 g) and hydroxybenzotriazole (1.29 g). After the mixture had been stirred for 3 hours, a solution of trans-4-amino-6-cyano-3,4-dihydro-2,2-dimethyl-2H-1-benzopyran-3-ol (2.00 g) and triethylamine (2.55 mL) in dimethyl formamide (20 mL) was added to it and the reaction mixture stirred overnight and allowed to attain room temperature. The reaction mixture was filtered and evaporated leaving a gum which was taken up in ethyl acetate and washed with brine and satd. sodium carbonate solution, before drying over anh. magnesium sulphate. Filtration and evaporation and recrystallisation from ethyl acetate gave dicyclohexylurea, and as a second crop the title compound (0.19 g) of mp 202°–204° C. The mother liquor contained a further (1.3 g) of product.

Mass spectrum: $M^+—H_2O$ at m/z 293.1167. Calcd for $C_{17}H_{15}N_3O_2$: 293.1164.

EXAMPLE 11

6-Cyano-3,4-dihydro-trans-4-(3-indolylcarbonylamino)-2,2-dimethyl-2H-1-benzopyran-3-ol

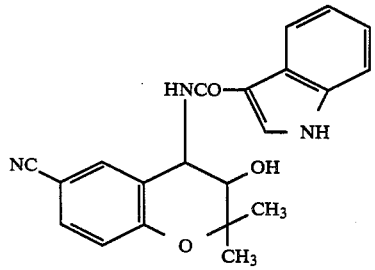
(E11)

The compound of example 11 was prepared in an analogous manner to the compound of example 7, using indole-3-carboxylic acid. The title compound was obtained as crystals from ethyl acetate: mp 219°–222° C.
NMR (CDCl$_3$-CD$_3$OD) δ:
1.36 (3H, s)
1.55 (3H, s)
3.78 (1H, d, J=10 Hz)
5.30 (1H, d, J=10 Hz)
6.91 (1H, d, J=10 Hz)
7.24 (2H, m)
7.67 (1H, narrow m)
7.93 (1H, s)
8.13 (1H, m)

EXAMPLE 12

6-Cyano-3,4-dihydro-trans-4-(4-hydroxybenzoylamino)-2,2-dimethyl-2H-1-benzopyran-3-ol

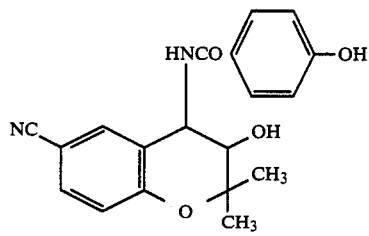
(E12)

The compound of example 12 was prepared in the same manner as the compound of example 10 using p-hydroxybenzoic acid, in dichloromethane as solvent. Column chromatography of the crude product gave the title compound as a white powder; m.p. 257°–261° C. after recrystallisation from ethyl acetatepentane.

Mass spectrum $M^+—H_2O$ at m/z 320.1157. Calcd for $C_{19}H_{16}N_2O_3$: 320.1161.

EXAMPLE 13

6-Acetyl-trans-4-(4-fluorobenzoylamino)-3,4-dihydro-2,2-dimethyl-2H-1-benzopyran-3-ol

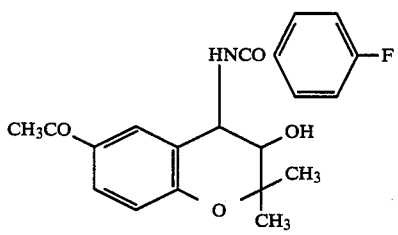
(E13)

This compound was prepared in an analogous manner to that of example 2 using p-fluorobenzoyl chloride. Recrystallisation of the product from ethyl acetate-pentane gave the title compound as the hemihydrate; m.p. 136°–140° C.

Mass spectrum $HM^+$ at m/z 358.1456. Calcd for $C_{18}H_{15}N_3O_2H^+$ 358.1454.

EXAMPLE 14

Trans-6-Cyano-3,4-dihydro-2,2-dimethyl-4-(3,4,5-trimethoxybenzoylamino)2H-1-benzopyran-3-ol

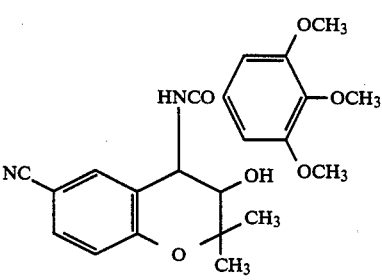
(E14)

The compound of example 14 was prepared in a similar manner to the compound of example 2, using 3,4,5-trimethoxybenzoyl chloride. The compound of this example was recrystallised from ethyl acetate; mp 177°–178° C.

Mass spectrum M+ at 412.1640. Calcd for $C_{22}H_{24}N_2O_6$: 412.1634.

PHARMACOLOGICAL DATA

Systolic blood pressure were recorded by a modification of the tail cuff method described by I M Claxton, M G Palfreyman, R H Poyser, R L Whiting, European Journal of Pharmacology, 37, 179 (1976). A W+W BP recorder, mode 8005, was used to display pulses Prior to all measurements rats were placed in a heated environment (33.5±0.5° C.) before transfer to a restraining cage. Each determination of blood pressure was the mean of at least 6 readings. Spontaneously hypertensive rats (ages 12–18 weeks) with systolic blood pressures >170 mmHg were considered hypertensive.

| Compound of Example 2 | Time Post Dose Hours | % Change in Systolic Blood Blood | % Change in Heart Rate |
|---|---|---|---|
| 6 rats | | | |
| Dose 1 mg/kg p.o. | 1 | −12 ± 2 | 4 ± 4 |
| | 2 | −12 ± 2 | 3 ± 6 |
| Initial Blood Pressure | 4 | −18 ± 2 | 2 ± 4 |
| 254 ± 4 mmHg | 6 | −19 ± 3 | 1 ± 1 |
| Initial Heart Rate | | | |
| 434 ± 17 beats/min | | | |

| Compound of Example 5 | Time Post Dose Hours | % Change in Systolic Blood Blood | % Change in Heart Rate |
|---|---|---|---|
| 6 rats | | | |
| Dose 1 mg/kg p.o. | 1 | −54 ± 6* | 7 ± 3 |
| | 2 | −53 ± 5* | 4 ± 5 |
| Initial Blood Pressure | 4 | −44** | −10 |
| 213 ± 7 mmHg | 6 | −30*** | −18 |
| Initial Heart Rate | | | |
| 473 ± 17 beats/min | | | |

*Only 4 rats had measurable pulses
**Only 2 rats had measurable pulses
***Only 1 rat had a measurable pulse

| Compound of Example 6 | Time Post Dose Hours | % Change in Systolic Blood Blood | % Change in Heart Rate |
|---|---|---|---|
| 6 rats | | | |
| Dose 10 mg/kg p.o. | 1 | −27 ± 6 | 1 ± 4 |
| | 2* | −28 ± 5 | −8 ± 1 |
| Initial Blood Pressure | 4* | −33 ± 4 | −6 ± 3 |
| 222 ± 5 mmHg | 6** | −35 ± 3 | −7 ± 1 |
| Initial Heart Rate | | | |
| 498 ± 13 beats/min | | | |

*1 rat had no measurable pulse
**2 rats had no measurable pulse

| Compound of Example 7 | Time Post Dose Hours | % Change in Systolic Blood Blood | % Change in Heart Rate |
|---|---|---|---|
| 6 rats | | | |
| Dose 1 mg/kg p.o. | 1 | −43 ± 7 | −1 ± 2 |
| | 2 | −29 ± 7 | −2 ± 2 |
| Initial Blood Pressure | 4* | −36 ± 4 | −10 ± 2 |
| 226 ± 7 mmHg | 6** | −23 | −9 |
| Initial Heart Rate | 24 | 10± 4 | −7 ± 3 |
| 490 ± 9 beats/min | | | |

*2 rats had no measurable pulse
**3 rats had no measurable pulse

TOXICITY

No toxic effects were observed in any of the above tests.

We claim:
1. A compound of formula (I):

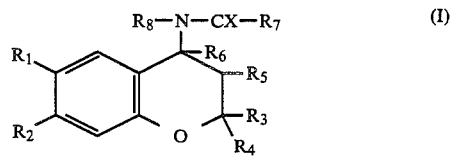

wherein:
either one of $R_1$ and $R_2$ is hydrogen and the other is selected from the class of $C_{1-6}$ alkylcarbonyl, $C_{1-6}$ alkoxycarbonyl, $C_{1-6}$ alkylcarbonyloxy, $C_{1-6}$ alkylhydroxymethyl, nitro, cyano, chloro, trifluoromethyl, $C_{1-6}$ alkylsulphinyl, $C_{1-6}$ alkylsulphonyl, $C_{1-6}$ alkoxysulphinyl, $C_{1-6}$ alkoxysulphonyl, $C_{1-6}$ alkylcarbonylamino, $C_{1-6}$ alkoxycarbonylamino, $C_{1-6}$ alkyl-thiocarbonyl, $C_{1-6}$ alkoxy-thiocarbonyl, $C_{1-6}$ alkyl-thiocarbonyloxy, 1-mercapto $C_{2-7}$ alkyl, formyl, or aminosulphinyl, aminosulphonyl or aminocarbonyl, the amino moiety being optionally substituted by one or two $C_{1-6}$ alkyl groups, or $C_{1-6}$ alkylsulphinylamino, $C_{1-6}$ alkylsulphonylamino, $C_{1-6}$ alkoxysulphinylamino or $C_{1-6}$ alkoxysulphonylamino, or ethylenyl terminally substituted by $C_{1-6}$ alkylcarbonyl, nitro or cyano, or —C($C_{1-6}$ alkyl)NOH or —C($C_{1-6}$ alkyl)NNH$_2$, or one of $R_1$ and $R_2$ is nitro, cyano or $C_{1-3}$ alkylcarbonyl and the other is methoxy or amino optionally substituted by one or two $C_{1-6}$ alkyl or by $C_{2-7}$ alkanoyl;
one of $R_3$ and $R_4$ is hydrogen or $C_{1-4}$ alkyl and the other is $C_{1-4}$ alkyl or $R_3$ and $R_4$ together are $C_{2-5}$ polymethylene;
either $R_5$ is hydrogen, hydroxy, $C_{1-6}$ alkoxy or $C_{1-7}$ carboxylic acyloxy and $R_6$ is hydrogen or $R_5$ and $R_6$ together are a bond;
$R_7$ is a member selected from the group consisting of phenyl, naphthyl, furanyl, thiophenyl, pyrryl, oxazolyl, thiazolyl, imidazolyl, thiadiazolyl, pyridinyl, pyridazinyl, pyrimidinyl, pyrazinyl, triazinyl, benzofuranyl, benzothiophenyl, indolyl, indazolyl, quinolinyl, isoquinolinyl or quinazoninyl said member being optionally substituted by one or more substituents selected from the group consisting of $C_{1-6}$ alkyl, $C_{1-6}$ alkoxy, hydroxy, halogen, trifluoromethyl, nitro, cyano, $C_{1-12}$ carboxylic acyl, and amino or aminocarbonyl optionally substituted by one or two $C_{1-6}$ alkyl;

$R_8$ is hydrogen or $C_{1-6}$ alkyl; and

X is oxygen or sulphur; the $R_8$-N-CX-$R_7$ group being trans to the $R_5$ group when $R_5$ is hydroxy, $C_{1-6}$ alkoxy or $C_{1-7}$ acyloxy; or a pharmaceutically acceptable salt or solvate thereof.

2. A compound according to claim 1, wherein one of $R_1$ and $R_2$ is hydrogen and the other is selected from the class of $C_{1-6}$ alkylcarbonyl, $C_{1-6}$ alkoxycarbonyl, nitro or cyano.

3. A compound according to claim 2, wherein one of $R_1$ and $R_2$ is hydrogen and the other is acetyl, nitro or cyano.

4. A compound according to claim 1, wherein $R_2$ is hydrogen.

5. A compound according to claim 1, wherein one of $R_1$ and $R_2$ is nitro, cyano or $C_{1-3}$ alkylcarbonyl and the other is amino optionally substituted by one or two $C_{1-6}$ alkyl or by $C_{2-7}$ alkanoyl.

6. A compound according to claim 1, wherein $R_1$ is nitro, cyano or $C_{1-3}$ alkylcarbonyl.

7. A compound according to claim 1, wherein the alkyl groups or alkyl moieties of alkyl-containing groups for $R_1$ and $R_2$ are methyl or ethyl.

8. A compound according to claim 1, wherein $R_3$ and $R_4$ are both methyl.

9. A compound according to claim 1, wherein $R_5$ and $R_6$ together are a bond.

10. A compound according to claim 1, wherein $R_5$ and $R_6$ are both hydrogen.

11. A compound according to claim 1, wherein $R_5$ is hydroxy and $R_6$ is hydrogen.

12. A compound according to claim 1, wherein $R_7$ is said optionally substituted phenyl or naphthyl.

13. A compound according to claim 1, wherein $R_7$ is other than the optionally substituted phenyl or naphthyl.

14. A compound according to claim 1, wherein said member is 2- or 3-furanyl, 2- or 3-pyrryl, 2- or 3-thiophenyl, 2-, 3- or 4-pyridinyl, 2- or 3-benzofuranyl, 2- or 3-benzothiophenyl, 2- or 3-indolyl, or 2- or 3-quinolinyl.

15. A compound according to claim 1, wherein the number of substituents for optional substitution of said member is one, two, three or four.

16. A compound according to claim 1, wherein the substituents for optional substitution of said member are selected from the group consisting of methyl, methoxy, hydroxy, chloro, nitro and cyano.

17. A compound according to claim 1, wherein said member is optionally substituted by one, two, three or four substituents selected from the group consisting of $C_{1-6}$ alkyl, $C_{1-6}$ alkoxy, halogen, trifluoromethyl, nitro and cyano.

18. A compound according to claim 1, wherein $R_7$ is phenyl, 4-hydroxyphenyl, 4-fluorophenyl, 4-cyanophenyl, 3-nitrophenyl, 3,4-dichlorophenyl or 3,4,5-trimethoxyphenyl.

19. A compound according to claim 1, wherein $R_7$ is unsubstituted 2- or 3-furanyl, unsubstituted 2- or 3-pyrryl, unsubstituted 2- or 3-thiophenyl, unsubstituted 2-, 3- or 4-pyridinyl, unsubstituted 2- or 3-benzofuranyl, unsubstituted 2- or 3-benzothiophenyl, unsubstituted 2- or 3-indolyl, or unsubstituted 2- or 3-quinolinyl.

20. A compound according to claim 1, wherein $R_8$ is hydrogen.

21. Trans-4-(4-cyanobenzoylamino)-6-cyano-3,4-dihydro-2,2-dimethyl-2H-1-benzopyran-3-ol;

Trans-4-(3,4-dichlorobenzoylamino)-6-cyano-3,4-dihydro-2,2-dimethyl-2H-1-benzopyran-3-ol;

Trans-4-(2-naphthoylamino)-6-cyano-3,4-dihydro-2,2-dimethyl-2H-1-benzopyran-3-ol;

Trans-4-(1-naphthoylamino)-6-cyano-3,4-dihydro-2,2-dimethyl-2H-1-benzopyran-3-ol;

Trans-4-(3-indolylcarbonylamino)-6-cyano-3,4-dihydro-2,2-dimethyl-2H-1-benzopyran-3-ol;

Trans-4-(4-hydroxybenzoylamino)-6-cyano-3,4-dihydro-2,2-dimethyl-2H-1-benzopyran-3-ol; or Trans-4-(3,4,5-trimethoxybenzoylamino)-6-cyano-3,4-dihydro-2,2-dimethyl-2H-1-benzopyran-3-ol.

22. Trans-4-benzoylamino-6-cyano-3,4-dihydro-2,2-dimethyl-2H-1-benzopyran-3-ol;

Trans-4-(3-nitrobenzoylamino)-6-cyano-3,4-dihydro-2,2-dimethyl-2H-1-benzopyran-3-ol;

Trans-4-(2-furanoylamino)-6-cyano-3,4-dihydro-2,2-dimethyl-2H-1-benzopyran-3-ol;

Trans-4-(3-pyridinylcarbonylamino)-6-cyano-3,4-dihydro-2,2-dimethyl-2H-1-benzopyran-3-ol;

Trans-4-(2-pyridinylcarbonylamino)-6-cyano-3,4-dihyro-2,2-dimethyl-2H-1-benzopyran-3-ol;

Trans-4-(3-furanoylamino)-6-cyano-3,4-dihydro-2,2-dimethyl-2H-1-benzopyran-3-ol;

Trans-4-(2-pyrrylcarbonylamino)-6-cyano-3,4-dihydro-2,2-dimethyl-2H-1-benzopyran-3-ol; or Trans-4-(4-fluorobenzoylamino)-6-acetyl-3,4-dihydro-2,2-dimethyl-2H-1-benzopyran-3-ol.

23. An anti-hypertensive pharmaceutical composition which comprises an anti-hypertensive effective amount of a compound according to claim 1, or a pharmaceutically acceptable salt or solvate thereof and a pharmaceutically acceptable carrier.

24. A method of treating or preventing hypertension in mammals, which comprises administering to the patient an anti-hypertensive effective amount of a compound according to claim 1, or a pharmaceutically acceptable salt or solvate thereof.

* * * * *